United States Patent [19]

Pelton

[11] Patent Number: 4,624,128
[45] Date of Patent: Nov. 25, 1986

[54] HYDROGEN PROBE

[75] Inventor: John F. Pelton, Yorktown, N.Y.

[73] Assignee: Union Carbide Corporation, Danbury, Conn.

[21] Appl. No.: 746,086

[22] Filed: Jun. 18, 1985

[51] Int. Cl.[4] .............................................. G01N 7/10
[52] U.S. Cl. ....................................................... 73/19
[58] Field of Search .................... 73/19, 23; 55/158; 75/93 E

[56] References Cited

U.S. PATENT DOCUMENTS

| | | | |
|---|---|---|---|
| 3,870,511 | 3/1975 | Szekely | 75/93 E |
| 3,941,566 | 3/1976 | Roche | 73/19 |
| 4,047,965 | 9/1977 | Karst et al. | 501/128 |
| 4,454,748 | 6/1984 | Terai et al. | 73/19 |

FOREIGN PATENT DOCUMENTS

| | | | |
|---|---|---|---|
| 684865 | 12/1952 | United Kingdom | 73/19 |
| 821821 | 10/1959 | United Kingdom | 73/19 |

OTHER PUBLICATIONS

C. E. Ransley et al., "An Instrument for Measuring the Gas Content of Aluminum Alloys During Melting and Casting", *Journal of Inst. of Metals*, vol. 86, pp. 212-219, 1957-1958.

*Primary Examiner*—Stephen A. Kreitman
*Attorney, Agent, or Firm*—A. H. Fritschler

[57] ABSTRACT

A probe for measuring hydrogen in aluminum melts includes straight inner and outer tubes, the latter having upper and lower plugs and a ceramic fiber sleeve in contact with said upper plug, a straight, ceramic blanketed third tube surrounding said plugs and preventing melt from passing therethrough.

1 Claim, 1 Drawing Figure

U.S. Patent  Nov. 25, 1986  4,624,128
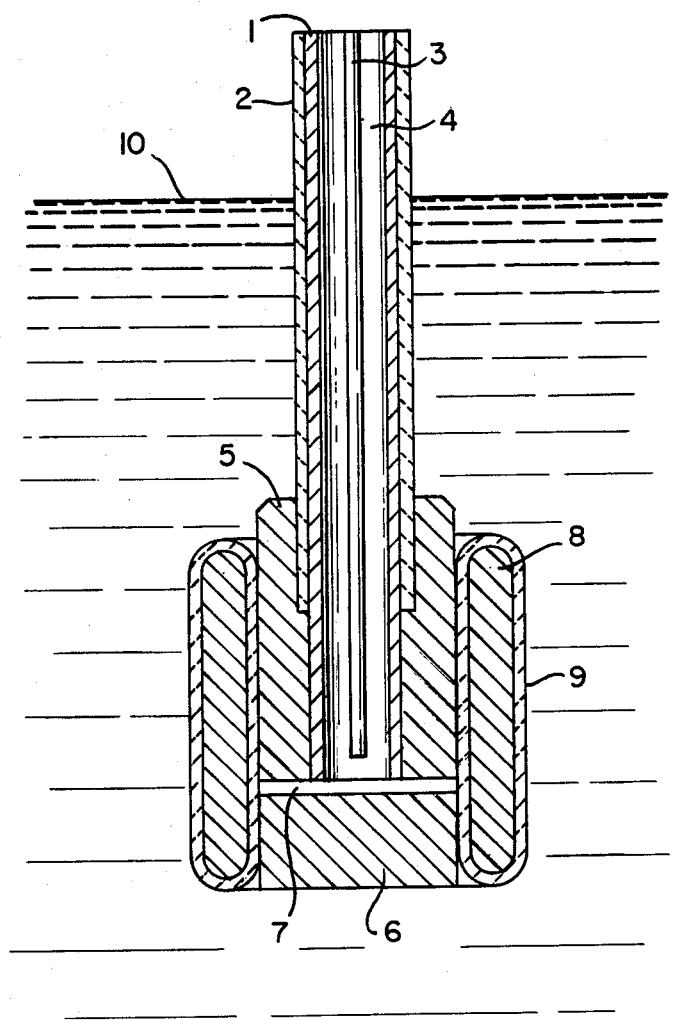

4,624,128

HYDROGEN PROBE

DESCRIPTION

1. Technical Field

This invention relates to a device for measuring the content of hydrogen in molten aluminum.

2. Background Art

An important quality of molten aluminum is its dissolved hydrogen content, and it is frequently necessary to know what this is before the metal is cast.

The hydrogen content may be measured by removing a sample of molten aluminum, allowing it to solidify and then analyzing for hydrogen by one of several commercial methods. These analyses are quite lengthy resulting in the data being obtained long after the metal is cast. Another method for measuring hydrogen content is to put a small sample of molten metal in a vacuum chamber and then observe the bubbles of hydrogen coming to the surface as the metal cools and solidifies. A sample solidified under vacuum can also be evaluated for density or porosity. While vacuum freeze methods such as those related give relatively rapid results, the values obtained are greatly affected by the nature and amount of particulate material in the metal.

It is desirable, then, to have a method for measuring hydrogen content directly in the molten aluminum, unaffected by particulate content. Such a direct in-situ process is described by Ransley et al in an article entitled "An Instrument for Measuring the Gas Content of Aluminum Alloys During Melting and Casting" published in the *Journal of the Institute of Metals,* Volume 86, 1957–58, pages 212 to 219, which is incorporated by reference herein.

In this in-situ method, a very small amount of an inert gas is circulated in a closed loop. During part of its travel, the inert gas is brought into contact with a molten aluminum free-surface in a submerged location. The gas is then circulated through a gas analyzer, which measures the hydrogen content by changes in thermal conductivity, and then back to the molten aluminum contact zone. Hydrogen diffuses from the molten aluminum into the inert gas until it reaches a partial pressure, which is in equilibrium with the hydrogen in the molten aluminum. At this point, the gas analyzer output is noted and is converted to hydrogen partial pressure (by previous calibration). This partial pressure can then be converted to hydrogen content by reference to a previously determined solubility of hydrogen in the molten aluminum being tested. The relationship between hydrogen solibility and temperature is given by Ransley et. al. for pure aluminum as:

$$\log_{10} S = -(2760/T) + 2.765 \quad \text{(i)}$$

Wherein S = the solubility of hydrogen at 760 millimeters in cubic centimeters S.T.P. per 100 grams of aluminum; and T = temperature in degrees Kelvin.

S.T.P. = standard temperature and pressure.

For hydrogen pressures other than 760 millimeters, the solubility is given by the equation $$S = S_o[(P/760)]^{\frac{1}{2}} \quad \text{ii}$$

wherein S = the solubility of hydrogen at the pressure of interest in cubic centimeters S.T.P. per 100 grams of aluminum;

$S_o = S$ as determined in equation (i) above; and

P = partial pressure of hydrogen in millimeters of mercury.

The primary problem with this process is the probe, which is used to carry it out. An all metal probe is rapidly dissolved in aluminum. Such a probe can be protected by a ceramic enamel, but this is not a practical solution from a production point of view. A dense alumina or alumina-silica probe stem is easily damaged by thermal shock. While thermal shock can be reduced by coating with a loose layer of alumina grains, the stem is still very delicate. In addition to being easily broken, such probes can develop cracks that are not visible on examination. These cracks lead to erratic readings.

It has also been found that the thermal shock coatings provide a gas diffusion path around the shroud of the probe and up the stem to the surface. Hydrogen which has diffused from the metal into the circulating gas stream can escape by diffusing up the stem, thus preventing the system from every reaching equilibrium. This causes the probe to give low readings. While this can be corrected for to some extent, the amount of error is not constant. The degree of inconsistency depends on the degree of turbulence in the molten metal surrounding the probe. Not only does hydrogen escape up the probe, but atmospheric gases can diffuse down the probe. This leads to various other errors. When argon is used as the inert circulating gas in the probe (e.g., when making measurements in aluminum which has argon bubbles in it), nitrogen diffuses down the stem from the air above giving erroneous high readings. Oxygen diffusing down the stem can also cause erratic low readings under some circumstances. While the effects of atmospheric gas diffusion can be eliminated by using a shield around the probe, the shield can raise complications such as the need for another metered inert gas flow and the need to observe proper immersion of the shield. The material problems that exist for probes also exist for shields.

DISCLOSURE OF THE INVENTION

An object of this invention, therefore, is to provide a probe for measuring the content of hydrogen in molten aluminum, which is (a) accurate under essentially all operating conditions; (b) not easily damaged particularly with respect to damage which is not readily apparent to the technician, but is responsible for erratic results; and (c) practical to produce.

Other objects and advantages will become apparent hereinafter.

According to the present invention, a probe for measuring the content of hydrogen in molten aluminum or alloys thereof has been discovered comprising the following components in combination:

(i) a straight first tube open at both ends;

(ii) a straight second tube open at both ends and fixed within the first tube in such a manner that a passage is provided between the outer wall of the second tube and the inner wall of the first tube;

(iii) a woven ceramic fiber sleeve surrounding, and in contact with, part of the first tube, the sleeve running from above the uppermost point of the first tube exposed to the melt to a point between the uppermost point of the upper plug referred to as component (iv) and the lower end of the first tube;

(iv) an upper plug surrounding the bottom portion, but not the end, of the first tube, the upper part of the plug being in contact with the lower part of the sleeve and the lower part of the plug being in such close contact with the first tube that gas is essentially unable to pass therethrough;

(v) a lower plug bearing a spaced and fixed relationship to the lower open ends of the upper plug and the first tube; and (vi) a straight third tube, open at both ends, having a woven ceramic blanket covering the outer wall, and at least those portions at each end of the inner wall, thereof, the blanketed third tube surrounding, and in contact with, the upper and lower plugs wherein the contact between the blanketed third tube and upper and the lower plugs is so close that the melt is essentially unable to pass therethrough.

BRIEF DESCRIPTION OF THE DRAWING

The sole FIGURE of the drawing is a schematic diagram of an embodiment of the hydrogen probe.

DETAILED DESCRIPTION

Referring to the drawing:

First tube 1, which may be referred to as the outer tube or stem, is covered with a woven ceramic fiber sleeve 2 from a point above that at which the probe resides in the molten aluminum. The term "aluminum" is considered to mean aluminum and alloys of aluminum. Sleeve 2 runs from that point down first tube 1 to a point below the uppermost end of upper plug 5.

First tube 1 is open at both ends and may be straight or bent. Generally, the probe is inserted in the melt vertically, positioned as shown in the drawing. Within first tube 1 is second tube 3. There is a passage 4 between the inner wall of first tube 1 and the outer wall of second tube 3. Second tube 3 may be referred to as the inner tube. It is also open at both ends and straight. The lower end of second tube 3 usually does not quite reach the lower end of first tube 1.

Upper (or transition) plug 5 surrounds the lower portion of first tube 1 with the upper part being recessed in order to accommodate the thickness of sleeve 2 and yet provide a tight fit and the lower part being snugly fitted to first tube 1. The fit should be tight enough to essentially prevent the passage of gas in either direction.

Lower (or bottom) plug 6 fits just below the lower ends of upper plug 5 and first tube 1. A small space 7 is left in between.

Finally, there is third tube 8, which is blanketed with the same or similar woven ceramic fiber as used in sleeve 2 (referred to as blanket 9). Blanketed third tube 8 surrounds and is in contact with upper plug 5 and lower plug 6. All of the parts are held tightly together by friction, which may be assisted by the use of ridges and grooves or protrusions and recesses. The tight fit can be accomplished by press fitting. The contact between blanketed tube 8, upper plug 5, and lower plug 6 is close enough to essentially prevent the passage of molten aluminum. The surface of the molten aluminum is designated as melt level 10. This gives an indication as to where the probe will usually be placed in the melt.

As noted, first tube 1 and third tube 8 are covered with a woven ceramic fiber. The material is such that it is not readily wetted by molten aluminum. Examples of ceramic fibers, which can be used in subject device, are an alumina-silica ceramic fiber having a diameter of 10 to 13 microns (manufactured by Minnesota Mining and Mfg. Co. under the trademark NEXTEL 312), which is preferred, other alumina-silica and glass fibers for high temperature use, and vitreous silica. Alumina-silica fibers useful in subject process are described in U.S. Pat. No. 4,047,965, to Karst et al, which is incorporated by reference herein. The high surface tension of the molten aluminum keeps it from penetrating most of the small openings between the fibers. Thus, the metal of which the bulk of the probe is made is protected from the corrosive action of the aluminum and gas spaces are provided within the ceramic fiber weave.

The spaces within the ceramic fiber weave of blanket 9 provide a zone for the transfer of hydrogen from the molten aluminum to a gas residing in these spaces. The hydrogen mixes with this gas and then diffuses into space (or zone) 7. The inert gas that is circulated through the probe enters this same space 7 by flowing down space 4. The inert gas then flows from space 7 up second tube 3. The flow can be reversed, if desired, i.e., the inert gas in flow down second tube 3 to space 7 are then up space 4. This inert gas picks up the hydrogen that has diffused into space 7 from the outer surface of third tube 8.

Hydrogen can diffuse up the gas spaces in sleeve 2 and gases from the surface of the molten melt can diffuse down the spaces in sleeve 2. To keep this from affecting the operation of the probe, upper plug 5 is preferably constructed as shown in the drawing. The liquid aluminum wets upper plug 5 and this interrupts the diffusion path between first tube 1 and third tube 8. Further, first tube 1 is, desirably, press fitted into upper plug 5 and then essentially no gas passes from the outer surface of first tube 1 to space 7. The function of lower plug 6 is to hold blanket 9 in place and prevent molten aluminum from entering space 7.

The life of subject probe is limited by the slow attack of liquid aluminum on the metal parts of the probe where it penetrates the woven ceramic fiber with perforation of first tube 1 being the most likely limiting factor. This penetration can be reduced by impregnating the ceramic fiber with a slurry of fine alumina powder containing a small amount of colloidal silica or an organic/aluminum compound as a binder. The composition of the slurry is, typically, colloidal silica with a 10 percent solids content mixed with Buhler No. 40-6435 AB levitated alumina to provide a thin, brushable slurry. The slurry fills the larger openings between the strands of the woven ceramic fiber and reduces aluminum penetration. This treatment has two disadvantages. The first is that it reduces the response rate of the probe slightly. The second is that the tendency of the probe to retain moisture from humid air is increased, giving rise to a greater surge or overshoot in the probe reading when it is first inserted in the molten metal. This is not a problem, however, when the probe is to be continually submerged in the melt for long periods of time. In this case the slurry treatment is most beneficial because longer life is needed.

The other life limiting factor is erosion of upper plug 5, which is made of a material that is wetted by liquid aluminum in order to interrupt the gas diffusion path from space 7 to first tube 1 along its outer surface. It is preferably made of metal which provides strength, resistance to cracking, resistance to diffusion of hydrogen, and wettability by the molten aluminum. Gray cast iron is a preferred material for upper plug 5 because it is more resistant to erosion in molten aluminum than most other metals. Internally oxidized titanium should also serve well in this capacity although there will be some sacrifice in probe response rate. In any event, some erosion of upper plug 5 is allowable. As upper plug 5 is eroded, its upper end becomes recessed into third tube 8. As long as this recess is not so deep that it prevents rewetting of the upper surface of upper plug 5 by the molten aluminum, the probe will continue to operate properly.

The probe is, typically, used in the process, and with the apparatus, described in U.S. Pat. No. 3,870,511, which is incorporated by reference herein. In this patent, a technique for refining aluminum by sparging with an inert gas such as nitrogen or argon is described. Where argon is used as the sparging gas, bubbles of argon will frequently come into contact with third tube 8. If the probe recirculating gas is nitrogen, then the argon entering the system gives an artificially low reading because argon has a lower thermal conductivity than nitrogen. This error can be avoided by using argon as the circulating gas in the probe, i.e., it is preferred to use the same gas for both refining and hydrogen level determination provided that the gas is inert.

With the mode of operation using argon for both functions, however, any nitrogen entering the probe from the atmosphere will give an artificially high reading. This does not occur, however, to a measurable degree when measuring normal hydrogen levels, but, at very low hydrogen levels, there may be a slight error due to diffusion of nitrogen through first tube 1. This can be avoided by using a shield on first tube 1 above the melt level. A typical shield (not shown) is dimensionally similar to third tube 8. It has a cylindrical wall and is open at both ends. The upper end is sealed to outer tube 1 at a point just above the upper end of sleeve 2. The lower end is just below melt level 10. The shield is sized so that there is an annular space between its wall and the outer surface of sleeve 2/outer tube 1. At the top of the shield is an inlet port for an inert shield gas. The shield gas passes through the annular space into the melt. Disadvantages of the shield were noted above.

Except for the ceramic fiber and lower plug 6, the components of subject probe are preferably made of metal. While upper plug 5 may be made of cast iron or titanium, as noted above, the other metal components are usually made of stainless steel, e.g., AISI 304 or 321. The object, of course, is to provide materials which will withstand the corrosive action of molten aluminum, which, due to current refining techniques, is usually in motion. To this end, lower plug 6 is preferably made of graphite. All of the tubes and plugs are, preferably, cylindrical in shape. Further, it is preferred to keep the internal volume of first tube 1 and second tube 2 as low as possible consistent with a reasonable pressure drop in the gas circulating system of the probe. The lower the total of gas volume in the system, the faster the probe response.

The drawing does not show a holder for the probe. The holder can be designed in various ways, but, typically, it is attached to the top of the probe and has small tubes, which connect inner tube 3 and the annular space between inner tube 3 and outer tube 1 through the holder to an analytical instrument. If a shield is needed to prevent atmospheric gases from passing down the outer surface of first tube 1, a titanium shield is recommended.

Typical dimensions are as follows: length of holder plus probe = 14 inches; length of probe = 13.5 inches; outer diameter of first tube 1 = 0.059 inch; wall thickness of first tube 1 = 0.009 inch; outer diameter of second tube 2 = 0.187 inch; wall thickness of second tube 2 = 0.058 inch; length of upper plug 5 = 1.5 inches; length of third tube 8 = 1.5 inches; length of lower plug 6 = 3/16 inch; thickness of sleeve 2 and blanket 9 = 0.030 inch; distance between upper plug 5 and lower plug 6, i.e., space 7 = 1/16 inch; outer diameter of upper plug 5 = 0.5 inch; outer diameter of third tube 8 = 0.75 inch; outer diameter of lower plug 6 = 0.5 inch. Number of inches of probe, which will be inserted in melt = 3 to 4 inches. The term "length" refers to measurement from top to bottom in the vertical position as shown in drawing.

I claim:

1. A probe for measuring the content of hydrogen in a melt containing aluminum or alloys thereof comprising the following components in combination:
    (i) a straight first tube open at both ends;
    (ii) a straight second tube open at both ends and fixed within the first tube in such a manner that a passage is provided between the outer wall of the second tube and the inner wall of the first tube;
    (iii) a woven ceramic fiber sleeve surrounding, and in contact with, part of the first tube, the sleeve running from above the uppermost point of the first tube exposed to the melt to a point between the uppermost point of the upper plug referred to as component (iv) and the lower end of the first tube;
    (iv) an upper plug surrounding the bottom portion, but not the lower open end, of the first tube, the upper part of the plug being in contact with the lower part of the sleeve and the lower part of the plug being in such close contact with the first tube that gas is essentially unable to pass therethrough;
    (v) a lower plug bearing a spaced and fixed relationship to the lower open ends of the upper plug and the first tube; and
    (vi) a straight third tube, open at both ends, having a woven ceramic blanket covering the outer wall, and at least those portions at each end of the inner wall, thereof, the blanketed third tube surrounding, and in contact with the upper and lower plugs wherein the contact between the blanketed third tube and the upper and lower plugs is so close that the melt is essentially unable to pass therethrough.

* * * * *